United States Patent
Ershadi et al.

(10) Patent No.: US 10,478,391 B2
(45) Date of Patent: Nov. 19, 2019

(54) SKIN-CARE FORMULATION FOR TREATING ANTI-AGING AND WRINKLE REDUCTION

(71) Applicants: Maryam Ershadi, Tarzana, CA (US); Emanuel Itzhakian, Tarzana, CA (US)

(72) Inventors: Maryam Ershadi, Tarzana, CA (US); Emanuel Itzhakian, Tarzana, CA (US)

(*) Notice: Subject to any disclaimer, the term of this patent is extended or adjusted under 35 U.S.C. 154(b) by 487 days.

(21) Appl. No.: 15/175,461

(22) Filed: Jun. 7, 2016

(65) Prior Publication Data

US 2016/0354299 A1   Dec. 8, 2016

Related U.S. Application Data

(60) Provisional application No. 62/172,723, filed on Jun. 8, 2015.

(51) Int. Cl.

| | | |
|---|---|---|
| A61K 36/00 | (2006.01) | |
| A61K 35/64 | (2015.01) | |
| A61K 35/644 | (2015.01) | |
| A61K 8/64 | (2006.01) | |
| A61K 8/34 | (2006.01) | |
| A61K 8/19 | (2006.01) | |
| A61K 8/49 | (2006.01) | |
| A61K 8/97 | (2017.01) | |
| A61K 8/98 | (2006.01) | |
| A61K 8/73 | (2006.01) | |
| A61K 8/44 | (2006.01) | |
| A61Q 19/08 | (2006.01) | |

(52) U.S. Cl.
CPC ............ *A61K 8/64* (2013.01); *A61K 8/19* (2013.01); *A61K 8/345* (2013.01); *A61K 8/44* (2013.01); *A61K 8/4946* (2013.01); *A61K 8/73* (2013.01); *A61K 8/735* (2013.01); *A61K 8/97* (2013.01); *A61K 8/987* (2013.01); *A61K 8/988* (2013.01); *A61Q 19/08* (2013.01); *A61K 2800/59* (2013.01)

(58) Field of Classification Search
None
See application file for complete search history.

(56) References Cited

U.S. PATENT DOCUMENTS

| | | | |
|---|---|---|---|
| 7,544,375 B1 * | 6/2009 | Bellin | A61K 36/00 424/401 |
| 9,849,077 B2 * | 12/2017 | Gan | A61K 8/8141 |
| 2010/0215726 A1 * | 8/2010 | Roth | A61K 8/64 424/450 |
| 2012/0015064 A1 * | 1/2012 | Burke-Colvin | A61K 8/585 424/777 |
| 2016/0206552 A1 * | 7/2016 | Mitchell | A61Q 19/00 |
| 2018/0133140 A1 * | 5/2018 | Zecchino | A61K 8/362 |

OTHER PUBLICATIONS

The website article of "Beauty Med EGF Serum" (https://www.bebeautifulskincare.com/Beauty-Med-EGF-Serum.html) copyrighted 2009-2019 (Year: 2009).*

* cited by examiner

*Primary Examiner* — Michael Barker
*Assistant Examiner* — Randall Winston
(74) *Attorney, Agent, or Firm* — Chen Huang; Adli Law Group P.C.

(57) ABSTRACT

The present disclosure relates to skincare products for treating the aging related issues of wrinkles or accidents such as scarring or burning and more specifically to specific formulations used to improve user outcomes in regards to skin elasticity, appearance and/or hydration. The contemplated products relate to formulations including combinations of biomimetic peptides and proteins of naturally occurring venoms in various known wildlife including bees, wasps, snakes, or snails, in a single formulation or in combination with various plant related ingredients with various carrier and/or medicament ability.

7 Claims, No Drawings

SKIN-CARE FORMULATION FOR TREATING ANTI-AGING AND WRINKLE REDUCTION

CROSS-REFERENCE TO RELATED PATENT APPLICATIONS

Embodiments of the present invention relate to U.S. Provisional Application Ser. No. 62/172,723, filed Jun. 8, 2015, entitled "SKIN-CARE FORMULATION FOR TREATING ANTI-AGING AND WRINKLE REDUCTION", the contents of which are incorporated by reference herein in its entirety and which is a basis for a claim of priority.

FIELD OF THE DISCLOSURE

The present invention is in the field of cosmetic formulations and more specifically cosmetic formulations related to the treatment or management of skin aging and wrinkle control, reduction or abatement.

BACKGROUND

Botox has been widely known and used in the art for about twenty years. Although effective for some people, botox has both some dangers and inadequacies for treating and/or ameliorating the aging and effects of aging of human skins. Presently, alternative biomimetic type proteins and peptides have been identified with varying degrees of success in assisting the anti-aging and/or anti-wrinkle. However, a combined product that may be used in lower doses or to treat a problem through multiple similar but physiologically different pathways at one time is still lacking. Thus, it would be ideal to provide new formulation that can achieve a significant decrease in skin aging and wrinkles.

The present disclosure solves the shortcomings of the prior art by providing a combination therapeutic cosmetic that incorporates a plurality of biomimetic peptides with known skin treatment effects into a single optimized formulation capable of treating skin aging and wrinkle problem more efficiently and/or through a combination of physiological pathways and responses.

SUMMARY OF THE DISCLOSURE

The embodiments of the present invention generally relate to skin care products treating the aging related issues of wrinkles or accidents such as scarring or burning and more specifically to specific formulations used to improve user outcomes in regards to skin elasticity, appearance and/or hydration.

Additional embodiments include formulations or formulations for managing the aging process of skin in one product and additionally is comprised of a combination of venoms and/or their biometic protein or peptide equivalents into a single formulation for enhanced results.

Further embodiments comprise of an optimized formulation of at least two known biomimetic compounds derived from naturally occurring venoms in various known wildlife including bees, wasps, snakes, or snails, in a single formulation or in combination with various plant related ingredients with various carrier and/or medicament ability.

One exemplary formulation comprises a therapeutically effective amount of apitoxin (e.g, bee venom), a therapeutically effective amount of Glycerin, Aqua, Dipeptide Diaminobutyroyl Benzylamide Diacetate (e.g., SYN®-AKE), and a therapeutically effective amount of µconotoxin CnCIII (e.g., XEP™-018) admixed in a single formulation. The formulation may optionally include various carriers, chelator, diluent, emollient, emulsifier, stabilizers and enhancement additives, such as aloe vera which is known to help protect the skin and Alp Rose extract which is known to support epidermal regeneration. Additional amino acids, antioxidants and vitamins such as B and C are contemplated for use in the present invention.

Additionally, various carrier type ingredients may be added in order to assist the uptake of the formulation in the contemplated layer of the skin to be treated. For the purposes of the present invention a carrier is deemed any substance, chemical or solvent which assists with the active ingredient reaching the physiological destination intended for maximum therapeutic effect.

DETAILED DESCRIPTION OF THE DISCLOSURE

The advantages of the present invention include the ability to more effectively treat skin related problems such as aging and wrinkles with a combination approach that helps enhance efficacy by either creating better results or allowing for a lower dose of any one of the three venoms contemplated to be used than normally necessary for the same results. Thus by increasing the therapeutic ratio of any of the active compounds you increase the safety profile.

An exemplary physiological effect treated is mimic wrinkles which for the purposes of the present invention are defined as part of the visible face wrinkles. As time passes, these wrinkles persist permanently and get deeper and deeper: frown lines, laughter lines and crows feet lines appear more and more due to the repeated movements of facial muscles.

In accordance with one aspect of at least one embodiment of the present disclosure, a formulation is disclosed comprising: 1) a therapeutically effective amount of apitoxin (e.g, bee venom), 2) a therapeutically effective amount of Glycerin, Aqua, Dipeptide Diaminobutyroyl Benzylamide Diacetate (e.g., SYN®-AKE) or equivalent biomimetic peptide, and 3) a therapeutically effective amount of μconotoxin CnCIII (e.g., XEP™-018). Ideally, the therapeutically effective amount of apitoxin is between 0.01-1.00% (i.e., the percentage range) within the formulation, the therapeutically effective amount of Glycerin, Aqua, Dipeptide Diaminobutyroyl Benzylamide Diacetate is between 1.00-8.00% within the formulation, and the therapeutically effective amount of μconotoxin CnCIII is between 1.00-8.00% within the formulation. Preferably, the disclosed formulation should apply to a user's skin at least once per day for optimal results.

Apitoxin, or honey bee venom, is a bitter colorless liquid; its active portion a mixture of proteins, which causes local inflammation and acts as an anticoagulant. A honeybee can inject 0.1 mg of venom via its stinger. It may have similarities to sea nettle toxin. Glycerin, Aqua, Dipeptide Diaminobutyroyl Benzylamide Diacetate (e.g., SYN®-AKE) is an anti-wrinkle active compound based on a synthetic tripeptide that mimics the effect of Waglerin-1, a peptide that is found in the venom of the Temple Viper, *Tropidolaemus wagleri*. μconotoxin CnCIII is a synthetic tripeptide derivative that was developed based on snake venom research and peptide synthesis. Glycerin, Aqua, Dipeptide Diaminobutyroyl Benzylamide Diacetate has been developed as efficient smoothing and anti-wrinkle care particularly effective against expression lines by relaxing facial muscles. This active tripeptide acts in a manner similar to Waglerin 1, a neuromuscular blocking compound of the venom of the Temple Viper. Acting at the post synaptic membrane, glycerin, aqua, dipeptide diaminobutyroyl benzylamide diacetate is also a reversible antagonist of the muscular nicotinic acetylcholine receptor (mnAChR). The tri-peptide binds to the epsilon subunit of the mnAChR which prevents binding of acetylcholine to the receptor; consequently it remains closed. In the closed state, there is no uptake of sodium ions (Na+) and the muscles stay relaxed. The Glycerin, Aqua, Dipeptide Diaminobutyroyl Benzylamide Diacetate peptide acts by reducing muscle cell contraction, smoothing mimic wrinkles in a short period, and is reversible. It is useful in anti-aging products and wrinkle treatment products, especially those targeting expression lines. μconotoxin CnCIII (e.g., XEP™-018) is a biomimetic peptide that mimics that from snail cone venom or an equivalent in various formulations.

In one embodiment of the present disclosure, the disclosed formulation can further be enhanced by adding a therapeutically effective amount of at least one of the following ingredients: 1) allantoin, 2) Glycerin, Albizia Julibrissin Bark Extract, Darutoside (e.g., Beautifeye™), 3) Glycerin, Royal Jelly (e.g., Royal Jelly G.), 4) Glycerin, Aqua, Terminalia Ferdinandiana Fruit Extract (e.g., AF Superox-C™), 5) Water, Glycerin, Citrus Aurantium Dulcis Callus Culture Extract, Xanthan Gum (e.g., Citrustem™), 6) Magnesium Aspartate, Zinc Gluconate, Copper Gluconate (e.g., Sepitonic™ M3), 7) sH-Ogliopeptide-1 (e.g., Dermatein® EGF), 8) Rhododendron Ferrugineum Leaf Cell Culture Extract (e.g., PhytoCellTec™ Alp Rose), 9) sodium hyaluronate (e.g., hyaluronic acid), 10) honey extract, and/or 11) caviar extract.

Allantoin has several beneficial effects as an active ingredient in cosmetics, including: a moisturizing and keratolytic effect, increasing the water content of the extracellular matrix and enhancing the desquamation of upper layers of dead skin cells, increasing the smoothness of the skin; promoting cell proliferation and wound healing; and a soothing, anti-irritant, and skin protectant effect by forming complexes with irritant and sensitizing agents. Preferably, the therapeutically effective amount (or recommended use level) of allantoin is between 0.01-1.00% (percentage range) within the disclosed formulation.

Glycerin, Albizia Julibrissin Bark Extract, Darutoside (e.g., Beautifeye™) protects, strengthens and improves the dermis properties. By consolidating the fragile microvascular network and stimulating the detoxifying systems, it reduces capillary leakages and accumulation of glycotoxic pigments responsible for uneven coloration and fatigue appearance. It lifts the upper eyelid, reduces crow's feet wrinkles, fades away dark circles and diminishes puffiness. Preferably, the therapeutically effective amount of Glycerin, Albizia Julibrissin Bark Extract, Darutoside is between 1.00-10.00% (percentage range) within the disclosed formulation.

Glycerin, Royal Jelly (e.g., Royal Jelly G.) is a Glycerin suspension of Royal Jelly. Royal jelly is a fluid secretion produced by worker bees, to feed all the larvae in the hive during their first days of life. Fresh royal jelly tastes acid and resembles condensed milk. Royal jelly is one of the richest natural products in amino acids. Royal jelly is also rich in vitamins, minerals, especially in potassium, magnesium, calcium, iron, phosphorus, sulfur, manganese, silicon, lead and others. In cosmetics, royal jelly is the flagship ingredient in the anti-aging products of a number of companies. The cosmetic properties of Royal Jelly are skin regeneration activity, skin conditioning activity, antioxidant activity, antimicrobial activity, anti-inflammatory activity and regulatory activity on sebum secretion. Royal jelly is a renown ingredient of cosmetic creams, because it provides a younger and clearer appearance to the skin. It's anti-oxidant activity makes it useful to formulate cosmetic products aimed at the protection of skin and hair integrity against oxidative processes. Preferably, the therapeutically effective amount of Glycerin, Royal Jelly is between 0.01-3.00% (percentage range) within the disclosed formulation.

Glycerin, Aqua, Terminalia Ferdinandiana Fruit Extract (e.g., AF Superox-C™) is extremely useful in protecting both skin and hair from environmental damage. It provides powerful antioxidant/free radical scavenging support and protection from the effects of UV exposure and other environmental aggressors. This ingredient is ideal for anti-aging, anti-acne, sun care, hair care, cleansing, and skin lightening applications. Preferably, the therapeutically effective amount of Glycerin, Aqua, Terminalia Ferdinandiana Fruit Extract is between 0.01-6.00% (percentage range) within the disclosed formulation.

Water, Glycerin, Citrus Aurantium Dulcis Callus Culture Extract, Xanthan Gum (e.g., Citrustem™) is a natural, sustainable and environmentally responsible active obtained from orange stem cells with an anti-aging effect. It organizes the inner structure of the skin for a younger looking appearance. It also increases skin firmness, diminishes wrinkles and helps to recover the elasticity of the skin. Preferably, the therapeutically effective amount of Water, Glycerin, Citrus Aurantium Dulcis Callus Culture Extract, Xanthan Gum is between 0.20-6.00% (percentage range) within the disclosed formulation.

Magnesium Aspartate, Zinc Gluconate, Copper Gluconate (e.g., Sepitonic™ M3) is a multi-mineral active chrono energizer (zinc, copper, magnesium synergy) for skins. Optimization of cellular respiration to stimulate energy (ATP) and metabolic (DNA proteins) mediators. It is also an active ingredient booster, which has a radical scavenging effect to inhibit the cellular free radical formation. It can also be a bioenergizer for clear, fresh skin. Preferably, the therapeutically effective amount of Magnesium Aspartate, Zinc Gluconate, Copper Gluconate is between 0.01-3.00% (percentage range) within the disclosed formulation.

sH-Ogliopeptide-1 (e.g., Dermatein® EGF) is a synthetic peptide consisting of the amino acids lycine, glycine and histidine. It is produced by the fermentation of *E. coli*. When sH-Ogliopeptide-1 is applied to skin, its epidermal growth factor accelerates healing and increases the rate of skin renewal on aging skin for impressive anti-aging results. Preferably, the therapeutically effective amount of sH-Ogliopeptide-1 is between 0.05-0.8mg of 100 g within the disclosed formulation.

Rhododendron Ferrugineum Leaf Cell Culture Extract (e.g., PhytoCellTec™ Alp Rose) is a cosmetic ingredient based on stem cells of alpine rose leaves. It promotes the vitality and longevity of skin stem cells. It also strengthens the skin barrier, providing better protection to the skin against climate-induced stress. Preferably, the therapeutically effective amount of Rhododendron Ferrugineum Leaf Cell Culture Extract is between 0.01-1.00% (percentage range) within the disclosed formulation.

Sodium Hyaluronate (e.g., Hyaluronic Acid) is the salt form of Hyaluronic Acid, a water-binding ingredient that has the ability to fill the spaces between the connective fibers known as collagen and elastin. Hyaluronic Acid is often injected into the skin, and hydrates and separates the skin, allowing it to retain water and create a plumping effect. Sodium Hyaluronate has been used for miniaturization and wound healing. Because the skin naturally loses its water composition as it ages (going from 10%-20% water to less than 10%), Hyaluronic Acid and Sodium Hyaluronate can replace some of the water lost in the dermis, and potentially fight wrinkles and other signs of aging. Preferably, the therapeutically effective amount of Sodium Hyaluronate is between 0.10-3.00% (percentage range) within the disclosed formulation.

Honey extract is an effective ingredient for natural hydration of the skin. It helps to balance the skins moisture levels. It is also widely used in cosmetic product to reduce inflammation and aid in tissue health, making it great for sensitive skin types. Preferably, the therapeutically effective amount of honey extract is between 0.10-1.50% (percentage range) within the disclosed formulation.

Caviar extract has been known to offer anti-aging benefits, which may lead to a youthful, smooth complexion. Using a caviar-derived homogenate can improve the mitochondria function of the skin and has a positive impact on collagen synthesis. In other words, it helped to reduce the effects of aging skin. Caviar extract is also boosted with Vitamin A and D, along with a host of B vitamins (including B1, B2 and B6). As well, the antioxidant-rich extract contains amino acids, organic compounds which are known to strengthen the skin and hair. Preferably, the therapeutically effective amount of caviar extract is between 0.10-1.50% (percentage range) within the disclosed formulation.

In yet another embodiment of the present disclosure, the disclosed formulation further comprises at least one chelating agent (or chelator). In general, a chelate is a chemical compound composed of a metal ion and a chelating agent. A chelating agent is a substance whose molecules can form several bonds to a single metal ion. In other words, a chelating agent is a multidentate ligand. For example, Tetrasodium Glutamate Diacetate (e.g., Dissolvine GL-47-S), which is a high purity, versatile and readily biodegradable chelate based upon L-glutamic acid, a natural and renewable raw material, can be used in the disclosed formulation. Ideally, the percentage range for the chelating agent in the disclosed formulation is between 0.01-1.00% for optimal result.

In yet another embodiment of the present disclosure, the disclosed formulation further comprises at least one type of diluent, such as deionized water, to reduce the concentration for the disclosed formulation. Depending on how concentrating one wants the disclosed formulation to be, the ideal percentage range for the diluent in the disclosed formulation is 5-80%.

In yet another embodiment of the present disclosure, the disclosed formulation further comprises at least one type of emollient. In general, emollients are non-cosmetic moisturizers which come in the form of creams, ointments, lotions and gels. Emollients may help skin to feel more comfortable and less itchy. They keep the skin moist and flexible, helping to prevent cracks. Examples of emollient used by the present disclosure may include, but are not limited to, at least one of the followings: Caprylic/Capric Triglyceride (e.g., Endimulse 33V), Isononyl Isononanoate, Squalane (e.g., Neossance Squalane) and Pataua Oil (e.g, Oenocarpus Bataua Fruit Oil). Preferably, the percentage range for each emollient used in the disclosed formulation is 0.50-7.00% (E.g., 0.50-7.00% for Caprylic/Capric Triglyceride, 0.50-7.00% for Isononyl Isononanoate, 0.50%-4.00% for Squalane, 0.50%-5.00% for Oenocarpus Bataua Fruit Oil).

In yet another embodiment of the present disclosure, the disclosed formulation further comprises at least one type of emulsifier. Emulsifiers are usually used in creams and lotions to mix water with oils. Since water and oil do not mix but stay separated, an additional agent (emulsifier) is necessary to form a homogenous mixture keeping water and oil together. Examples of emulsifiers used by the present disclosure may include, but are not limited to, at least one of the followings: Hydrogenated Lecithin, C12-16 Alcohols, Palmitic Acid (e.g., Biophillic™ H) and Cetyl Alcohol, Glyceryl Stearate, PEG-75 Stearate, Ceteth-20, Steareth-2 (Emulium® Delta). Preferably, the percentage range for each emulsifier used in the disclosed formulation is 1.00-10.00% (e.g., 1.50-10.00% for Hydrogenated Lecithin, C12-16 Alcohols, Palmitic Acid and 1.00-8.00% for Cetyl Alcohol, Glyceryl Stearate, PEG-75 Stearate, Ceteth-20, Steareth-2).

In yet another embodiment of the present disclosure, the disclosed formulation further comprises at least one a type of fragrance. Fragrance is added to give the disclosed formulation a scent and also stabilize that scent. An example of fragrance used by the present disclosure is Porcelain Skin 2013100470. Preferably, the percentage range for the fragrance used in the disclosed formulation is 0.05-0.70%.

In yet another embodiment of the present disclosure, the disclosed formulation further comprises at least one a type of humectant. In general, humectant is a hygroscopic substance used to keep things moist. In cosmetics, humectant can be used in topical dosage forms to increase the solubility of a chemical compound's active ingredient(s), increasing the active ingredients' ability to penetrate skin, and/or its activity time. An example of humectant used by the present disclosure is Aloe Barbadensis (Aloe Vera) Leaf Juice (e.g., Terra-Pure™ Aloe Vera 200×). Preferably, the percentage range for the humectant used in the disclosed formulation is 0.01-1.00%.

In yet another embodiment of the present disclosure, the disclosed formulation further comprises at least one a type of neutralizer as pH adjuster. An example of neutralizer used by the present disclosure is Aminomethyl Propanol (e.g., AMP-Ultra™ PC 2000). Preferably, the percentage range for the neutralizer used in the disclosed formulation is 0.01-0.50%.

In yet another embodiment of the present disclosure, the disclosed formulation further comprises at least one a type of non-ionic surfactant/emulsifier. An example of non-ionic surfactant/emulsifier used by the present disclosure is Polysorbate 60. Preferably, the percentage range for the nonionic surfactant/emulsifier used in the disclosed formulation is 0.10-3.00%.

In yet another embodiment of the present disclosure, the disclosed formulation further comprises at least one a type of preservative to prevent microbial growth and spoiling of the disclosed formulation and also infection of the skin. An example of preservative used by the present disclosure is Propanediol, Ethylhexylglycerin, Caprylyl Glycol, Caprylhydroxamic Acid (e.g., Spectrastat™ OEL). Preferably, the percentage range for the preservative used in the disclosed formulation is 0.50-5.00%.

In yet another embodiment of the present disclosure, the disclosed formulation further comprises at least one a type of rheology modifier. Rheology modifiers are complex ingredients that help to bring about exacting viscosity and flow to cosmetic formulations. Examples of rheology modifier used by the present disclosure may include, but are not limited to, at least one of the followings: Xanthan Gum and Acrylates/C10-30 Alkyl Acrylate Crosspolymer (e.g., Carbopol® Ultrez 21). Preferably, the percentage range for each rheology modifier used in the disclosed formulation is 0.05-0.70% (e.g., 0.05-0.60% for Xanthan Gum and 0.10-0.70% for Acrylates/C10-30 Alkyl Acrylate Crosspolymer).

In yet another embodiment of the present disclosure, the disclosed formulation further comprises at least one a type of sensorial modifier/mattifying agent. An example of sensorial modifier/mattifying agent used by the present disclosure is Polymethylsilsesquioxane, Diamond Powder (e.g., Granpowder Lumiere-DP). Preferably, the percentage range for the sensorial modifier/mattifying agent used in the disclosed formulation is 0.10-3.00%.

Table 1 below is another exemplary formulation in accordance with one embodiment of the present disclosure.

TABLE 1

| # | RAW MATERIAL | INCI NAME | FUNCTION | PERCENTAGE RANGE |
|---|---|---|---|---|
| 1 | Spectrastat ™ OEL | Propanediol, Ethylhexylglycerin, Caprylyl Glycol, Caprylhydroxamic Acid | PRESERVATIVE | 1.5-2.2 |
| 2 | Xanthan Gum | Xanthan Gum | RHEOLOGY MODIFIER | 0.15-0.30 |
| 3 | Deionized Water | Deionized Water | DILUENT | 10.0-80.0 |
| 4 | Terra-Pure ™ *Aloe Vera* 200x | *Aloe Barbadensis* (*Aloe Vera*) Leaf Juice | HUMECTANT | 0.10-0.40 |
| 5 | Dissolvine ® GL-47-S | Tetrasodium Glutamate Diacetate | CHELATOR | 0.05-0.20 |
| 6 | Allantoin | Allantoin | FUNCTIONAL | 0.10-0.30 |
| 7 | Carbopol ® Ultrez 21 | Acrylates/C10-30 Alkyl Acrylate Crosspolymer | RHEOLOGY MODIFIER | 0.20-0.35 |
| 8 | Biophillic ™ H | Hydrogenated Lecithin, C12-16 Alcohols, Palmitic Acid | EMULSIFIER | 3.0-5.0 |
| 9 | Emulium ® Delta | Cetyl Alcohol, Glyceryl Stearate, PEG-75 Stearate, Ceteth-20, Steareth-2 | EMULSIFIER | 2.0-4.0 |
| 10 | Endimulse ® 33V | Caprylic/Capric Triglyceride | EMOLLIENT | 1.5-3.5 |
| 11 | Isononyl Isononanoate | Isononyl Isononanoate | EMOLLIENT | 1.5-3.5 |
| 12 | Polysorbate 60 | Polysorbate 60 | NON-IONIC SURFACTANT/ EMULSIFIER | 0.50-1.5 |
| 13 | Neossance ® Squalane | Squalane | EMOLLIENT | 1.0-2.0 |
| 14 | Pataua Oil | *Oenocarpus Bataua* Fruit Oil | EMOLLIENT | 1.5-2.5 |
| 15 | XEP ™-018 | μconotoxin CnCIII | FUNCTIONAL | 2.0-4.0 |
| 16 | Syn ®-Ake | Glycerin, Aqua, Dipeptide Diaminobutyroyl Benzylamide Diacetate | FUNCTIONAL | 2.0-4.0 |
| 17 | Beautifeye ™ | Glycerin, *Albizia Julibrissin* Bark Extract, Darutoside | FUNCTIONAL | 2.0-4.0 |
| 18 | Royal Jelly G. | Glycerin, Royal Jelly | FUNCTIONAL | 0.20-1.0 |
| 19 | AF Superox-C ™ | Glycerin, Aqua, *Terminalia Ferdinandiana* Fruit Extract | FUNCTIONAL | 1.0-3.0 |
| 20 | Bee Venom | apitoxin | FUNCTIONAL | 0.25-0.75 |
| 21 | Citrustem ™ | Water, Glycerin, *Citrus Aurantium Dulcis Callus* Culture Extract, Xanthan Gum | FUNCTIONAL | 0.75-3.00 |
| 22 | Sepitonic ™ M3 | Magnesium Aspartate, Zinc Gluconate, Copper Gluconate | FUNCTIONAL | 0.50-1.0 |
| 23 | Dermatein ® EGF | sH-Ogliopeptide-1 | FUNCTIONAL | 0.10-0.4 mg/ 100 g |
| 24 | PhytoCellTec ™ Alp Rose | *Rhododendron Ferrugineum* Leaf Cell Culture Extract | FUNCTIONAL | 0.20-0.40 |
| 25 | Hyaluronic Acid | Sodium Hyaluronate | FUNCTIONAL | 0.50-1.50 |
| 26 | Honey Extract | Honey Extract | FUNCTIONAL | 0.35-0.75 |
| 27 | Caviar Extract | Caviar Extract | FUNCTIONAL | 0.35-0.75 |
| 28 | Porcelain Skin 2013100470 | Fragrance | FRAGRANCE | 0.25-0.35 |
| 29 | AMP-Ultra ™ PC 2000 | Aminomethyl Propanol | NEUTRALIZER | 0.15-0.25 |
| 30 | Granpowder Lumiere-DP | Polymethylsilsesquioxane, Diamond Powder | SENSORIAL MODIFIER/ MATTIFYING AGENT | 0.50-1.50 |

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:

1. A formulation comprising:
apitoxin;
a combination of Glycerin, Aqua, Dipeptide Diaminobutyroyl Benzylamide Diacetate equivalent biomimetic peptide;
µconotoxin CnCIII;
a combination of Glycerin, Aqua, Terminalia Ferdinandiana Fruit Extract;
at least one chelating agent;
wherein the at least one chelating agent is Tetrasodium Glutamate Diacetate that has a percentage range of 0.01-1.00% within the formulation;
deionized water that has a percentage range of 5-80% within the formulation;
at least one type of emollient that has a percentage range of 0.50-7.00% within the formulation;
wherein the at least one type of emollient is selected from a list consisting of Caprylic/Capric Triglyceride, Isononyl Isononanoate, Squalane and Pataua Oil;
at least one type of emulsifier that has a percentage range of 1.00-10.00% within the formulation;
wherein the at least one type of emulsifier is Hydrogenated Lecithin, C12-16 Alcohols, Palmitic Acid or Cetyl Alcohol, Glyceryl Stearate, PEG-75 Stearate, Ceteth-20 , Steareth-2 or both:
at least one a type of humectant, at least one a type of neutralizer, at least one a type of non-ionic surfactant/emulsifier and at least one a type of preservative; and
at least one a type of rheology modifier and at least one a type of sensorial modifier or mattifying agent.

2. The formulation of claim 1, wherein the apitoxin has a percentage range of 0.01-1.00% within the formulation, the combination of Glycerin, Aqua, Dipeptide Diaminobutyroyl Benzylamide Diacetate has a percentage range of 1.00-8.00% within the formulation and the µconotoxin CnCIII has a percentage range of 1.00-8.00% within the formulation.

3. The formulation of claim 1, further comprises 1) a combination of Glycerin, Albizia Julibrissin Bark Extract, Darutoside, and 2) sH-Ogliopeptide-1.

4. The formulation of claim 3, wherein the combination of Glycerin, Albizia Julibrissin Bark Extract, Darutoside has a percentage range of 1.00-10.00% within the formulation and the sH-Ogliopeptide-1 has an amount of 0.05-0.8mg per 100g within the formulation.

5. A formulation comprising:
0. 01-1.00% of apitoxin;
1. 00-8.00% of a combination of Glycerin, Aqua, Dipeptide Diaminobutyroyl Benzylamide Diacetate;
1. 00-8.00% of µconotoxin CnCIII;
a combination of Glycerin, Albizia Julibrissin Bark Extract, Darutoside;
a combination of Glycerin, Aqua, Terminalia Ferdinandiana Fruit Extract;
sH-Ogliopeptide-1;
at least one type of emollient selected from a list consisting of Caprylic/Capric Triglyceride, Isononyl Isononanoate, Squalane and Pataua Oil; and
at least one type of emulsifier, at least one a type of humectant, at least one a type of neutralizer, at least one a type of non-ionic surfactant/emulsifier, at least one a type of preservative, at least one a type of rheology modifier and at least one a type of sensorial modifier or mattifying agent.

6. The formulation of claim 5, wherein the combination of Glycerin, Albizia Julibrissin Bark Extract, Darutoside has a percentage range of 1.00-10.00% within the formulation, the combination of Glycerin, Aqua, Terminalia Ferdinandiana Fruit Extract has a percentage range of 0.01-6.00% within the formulation, and the sH-Ogliopeptide-1 has an amount of 0.05-0.8 mg per 100 g within the formulation.

7. A formulation comprising:
0. 01-1.00% of apitoxin;
1. 00-8.00% of a combination of Glycerin, Aqua, Dipeptide Diaminobutyroyl Benzylamide Diacetate;
1. 00-8.00% of µconotoxin CnCIII;
1. 00-10.00% of a combination of Glycerin, Albizia Julibrissin Bark Extract, Darutoside;
0.01-6.00% of a combination of Glycerin, Aqua, Terminalia Ferdinandiana Fruit Extract;
0.05-0.8mg of sH-Ogliopeptide-1 per every 100 g of the formulation;
at least one type of emollient, at least one type of emulsifier, at least one a type of humectant, at least one a type of neutralizer, at least one a type of non-ionic surfactant/emulsifier, at least one a type of preservative, at least one a type of rheology modifier and at least one a type of sensorial modifier or mattifying agent; and
aloe vera, amino acids, antioxidants and vitamins.

* * * * *